(12) United States Patent
Pozzi

(10) Patent No.: US 6,276,930 B1
(45) Date of Patent: Aug. 21, 2001

(54) ORTHODONTIC AID

(75) Inventor: Alessandro Pozzi, Florence (IT)

(73) Assignee: Leone S.p.A. (IT)

( * ) Notice: Subject to any disclaimer, the term of this patent is extended or adjusted under 35 U.S.C. 154(b) by 0 days.

(21) Appl. No.: 09/443,724

(22) Filed: Nov. 19, 1999

Related U.S. Application Data

(63) Continuation-in-part of application No. 09/039,792, filed on Mar. 16, 1998, now abandoned.

(30) Foreign Application Priority Data

May 6, 1997 (IT) .................................................. F197U0066

(51) Int. Cl.[7] ........................................................ A61C 3/00
(52) U.S. Cl. .................................................................. 433/9
(58) Field of Search ........................... 433/8, 9, 10, 11, 433/12, 13, 14, 15, 16, 17

(56) References Cited

U.S. PATENT DOCUMENTS

| | | | |
|---|---|---|---|
| 4,068,379 | 1/1978 | Miller et al. | 433/9 |
| 4,100,678 | 7/1978 | Yatabe | 433/9 |
| 4,279,593 | 7/1981 | Röhlcke | 433/8 |
| 5,326,259 | 7/1994 | Röhlcke et al. | 433/8 |
| 5,556,276 | 9/1996 | Roman et al. | 433/8 |
| 5,595,484 | 1/1997 | Orikasa et al. | 433/8 |
| 5,622,494 | 4/1997 | Andreiko et al. | 433/9 |

*Primary Examiner*—John J. Wilson
(74) *Attorney, Agent, or Firm*—McGlew and Tuttle, P.C.

(57) ABSTRACT

Orthodontic bracket having a retention base for a respective tooth and identifying indicia in relation to the tooth for which the orthodontic aid is suitable. The indicia includes a sign provided on the back side of the retention base. The size of the indicia is at least 3 square millimeters. The indicia has substantially null depth with respect to the retention base, thus following the outer profile of the latter.

10 Claims, 2 Drawing Sheets

PRIOR ART

ORTHODONTIC AID

This is a CIP of application Ser. No. 09/039,792 filed Mar. 16, 1998, now abandoned and the entire disclosure of this prior application is considered to be part of the disclosure of the accompanying application and is hereby incorporated by reference therein.

FIELD OF THE INVENTION

The present invention relates to an orthodontic aid or bracket.

BACKGROUND OF THE INVENTION

It is known that the orthodontic aids used for correcting dental malformations basically consist of one or more bodies featuring seats for an orthodontic archwire in their inner part, which are wedded to a retention base, as to allow various operating orthodontic aids to be suitable for the same archiwire which extends along the arch subjected to therapeutical treatment.

The manufacturing of these orthodontic aids is diversified on account of the different shape of each tooth so that a single orthodontic aid corresponds to a respective tooth. For example, an orthodontic aid for the upper right eye-tooth is different from that for the upper left eye-tooth and so on.

At present, in order to identify orthodontic aids in relation to the teeth for which they are suitable, each orthodontic aid is usually marked with a corresponding sign which consists of a numerical abbreviation or of a colour dot positioned on the disto-gingival edge of the orthodontic aid as is clearly shown in FIG. 1 of the enclosed drawings wherein said codes consist of a "2" and of black dot foreseen on the tie wings (A) of the bodies wedded to the retention base (B). However, an identification code positioned on this edge of the orthodontic aid consequently becomes less perceptible and recognizable, being the surface available, the area of which is generally about 1 square millimeter, quite limited, which can cause tiredness and mistakes on the part of the orthodontist.

The U.S. Pat. No. 5,326,259 describes a method of manufacturing orthodontic aids with identifying indicia which can be positioned on the upper area of the bodies wedded to the retention base. But, despite its complexity, this common operative method presents the above mentioned disadvantages. Another example of such device is found in U.S. Pat. No. 5,556,276.

The U.S. Pat. No. 5,622,494 relates to a plastic orthodontic appliance having projecting structure extending outwardly from a bonding base which is shaped to have a bonding area within the bonding base and the free edge of the projecting structure. A portion of the bonding base may be an open area without projections to allow for the molding of an identifying mark.

However, this known appliance doesn't allow for molding identifying marks easily recognizable by the orthodontist. In fact, by increasing the marking area the bonding area will be correspondingly reduced with a relevant bonding action reduction. Furthermore, the molding of identifying marks is cause for a limited possibility of choice for the appliance bonding structure, said molding technique being not utilizable, for example, in case of brackets having bonding net-like structure, which are greatly reliable and fully tested, due to the fact that the molding techinique would imply a deformation of such entity to functionally damage the bonding net-like structure.

The U.S. Pat. No. 5,595,484 describes a plastic aesthetical orthodontic bracket. The retention base may be provided with identification marks which are molded in small recessed portions of the retention base to be not noticeable when the bracket is bonded to the relevant tooth. The molding of the identification marks in the small recesses of the lingual surface of the bracket may involve an undue visual weariness by part of the orthodontist because said marks are too small. Even in this case a bracket having a retention base with net-like structure is not utilizable because the molding techinique would imply an untollerable deformation of the net-like structure.

SUMMARY OF THE INVENTION

The object underlying the present invention is to overcome the aforesaid disadvantages.

This object has been achieved in accordance with the invention by manufacturing an orthodontic bracket having a retention base for a respective tooth and identifying indicia in relation to the tooth for which the orthodontic aid is suitable. The indicia includes a sign provided on the back side of the retention base. The size of the indicia is at least 3 square millimeters. The indicia has substantially null depth with respect to the retention base, thus following the outer profile of the latter.

The present invention has the advantage of rendering the identification code more easily recognizable in every operative condition without modifying the structure of the orthodontic aid and improving its hold while it is being used, all this in an easy, reliable and inexpensive manner.

Furthermore, the anchorage of the retention base to the tooth is not adversely affected, contrarly to the case of brackets having molded identification marks, since the thickness of the identification marks according to the invention is substantially null when compared with the thickness of the retention base and, therefore, it follows the outer profile of the latter without adversely affecting the shape and operative efficiency thereof.

A further advantage lies in that the marking may be carried out even separately from the manufacturing or assemblage of the bracket. Said marking may be also performed with appropriate inks, even for aesthetical plastic brackets.

BRIEF DESCRIPTION OF THE DRAWINGS

These and further advantages and characteristics of the present invention will be better understood by anyone skilled in the art from a reading of the following description in conjunction with the attached drawings, given as a practical exemplification of the invention, but not to be considered in a limitative sense, wherein.

DETAILED DESCRIPTION OF THE PREFERRED EMBODIMENT

Figure 1:
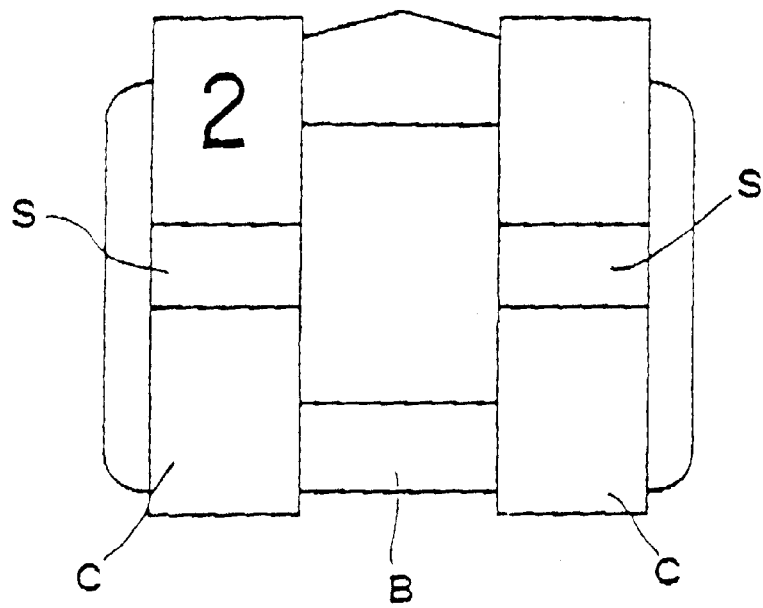
FIG. 1 is a plan view of an orthodontic aid with traditional identification codes.
Figure 2:
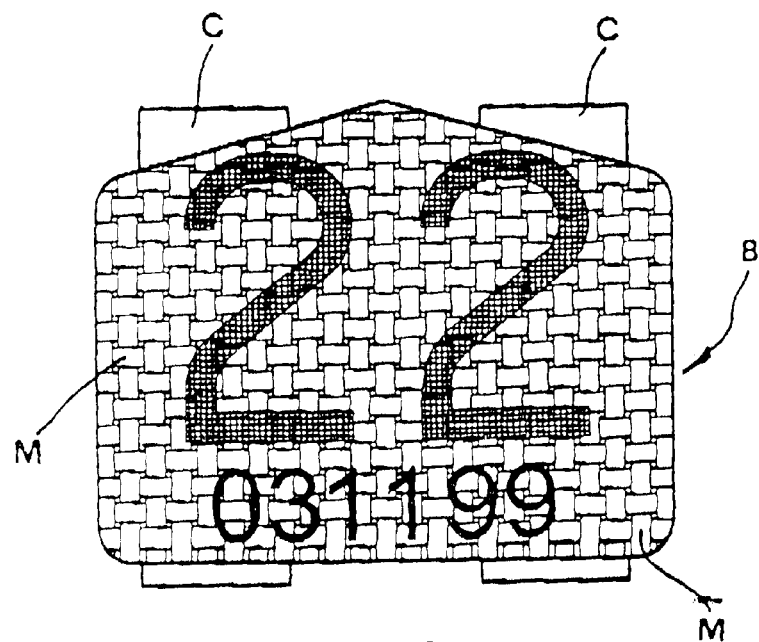
FIG. 2 is a back view of an orthodontic aid in accordance with the present invention.
Figure 3:
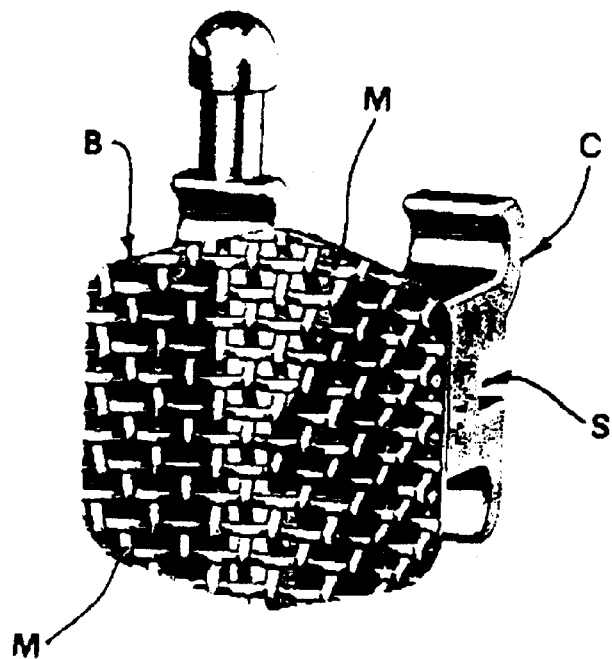
FIG. 3 is a perspective back view of an orthodontic aid in accordance with the present invention.

An orthodontic bracket in its essential structure and with reference to the figures of the enclosed drawings, in accordance with the invention, consists of a retention base (B) and of two bodies (C) wedded to the retention base and provided with seats for a corresponding section of an orthodontic archwire. The orthodontic aid is provided with indicia consisting of a numerical code ("22" in FIG. 2 and "14" in FIG. 3) provided on the back side of the retention base (B) that is to say on the side which will adhere to the tooth. In the examples of FIGS. 2 and 3, the code of the orthodontical aid corresponds to the position of the tooth for which it is suitable, in compliance with the "FDI SISTEM" identification system (i.e. FEDERATION DENTAIRE IINTERNATIONALE) wherein teeth can be identified thanks to a progressive numeration with two figures, always starting from the medium line, wherein the first ten indicates the upper right side, the second ten indicates the upper left side, the third ten indicates the lower left side and the fourth ten indicates the lower right side, as is shown in the chart below:

| 18 17 16 15 14 13 12 11 | 21 22 23 24 25 26 27 28 |
|---|---|
| 48 47 46 45 44 43 42 41 | 31 32 33 34 35 36 37 38 |

In this way, for example, the lower central incisors are identified by the numbers 41 and 31 and so on.

Any other identification system of the position of teeth can advantageously serve the purpose as well. To better explain this system and in accordance with a technique already known to technicians operating in this field, the aforementioned identification code may consist of a number with one figure identifying the tooth, proceded or followed by a "+" or a "−" sign, which indicates if the number belongs to the right or to the left side: the 3 + symbol identifies the upper right eye-tooth and the − 4 symbol identifies the first lower left premolar.

Anyway, whatever symbols may be chosen, the size of the indicia provided on the back side (B) is at least 3 square millimeters, for example 9 square millimeters, as to allow the orthodontist to better recognize it, to avoid getting tired and making mistakes and to execute the operation in a safe manner.

In FIG. 2 it is also shown a further code provided on the back side (B) of the orthodontic aid. Said further code may be, for example, a number ("031199") representing the manufacturing date or source.

The marking of the retention base (B) can be produced by means of a programmable laser apparatus which many technicians already know. The laser apparatus can be, for example, a diode-pumped laser of the "ROFIN SINAIR" type manufactured by the German firm Rofin Sinair Laser GmbH.

Figure 4:
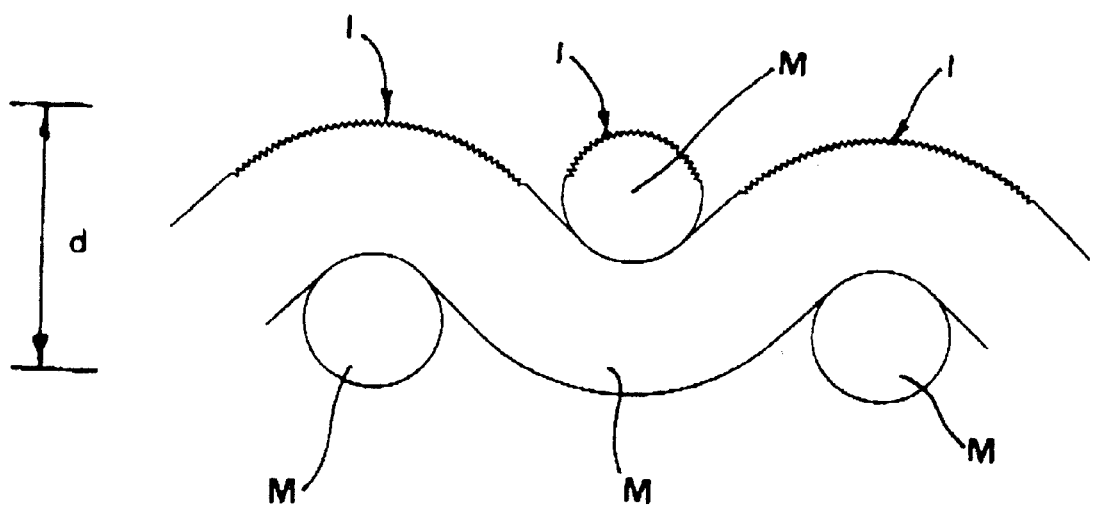
FIG. 4 is a schematic partial cross section of the net-like back side of an orthodontic aid in accordance with the present invention.

The orthodontic aid illustrated in FIGS. 2 and 3 and, partially, in FIG. 4, features a net-like retention base, but the present invention can be applied to orthodontic aids with various types of bases. The net-like base structure of the orthodontic aid in accordance with the present invention consists of individual mesh elements (M) in a lattice arrangement.

An orthodontic aid featuring a net-like retention base is known from U.S. Pat. No. 4,068,379 which also relates to manufacturing of orthodontic aids having a net-like back side.

The anchorage of the retention base (B) to the tooth can be effected in the usual manner, by applying adhesive or dental cement on the dental surface, which has previously been treated with acids facilitating the formation of microscopic leaks for a consequent better retention.

The marking of the indicia produced in accordance with the invention, by means of a laser beam or by equivalent means, allows the formation of a much wider area where adhesive can operate more effectively. As shown in FIG. 4, the elements (M) of net-like bass (B) are subject, due to the action of the laser apparatus operating the indicia marking, to an oxiding and/or roughening effect which leads to a wider adhesion area of the net-like structure with the adhesive or dental cement. The roughened portions of the elements (M) are those indicated in FIG. 4 by the letter "I".

It will be further appreciated that the indicia provided according to the present invention follow the outer profile of the net-like base (B), as it is visible in FIG. 3, and there are no projections from the latter which may limit the bonding of the orthodontic aid to the respective tooth.

According to the present invention, there is provided a structural modification of a portion of the back side of the retention base (B), said portion having the shape and size of the desired identifying indicia or code. The depth of the said structurally altered portion of the back side base (B) is substantially null with respect to the depth (d) of the same base (B). Said slight structural modification of the retention base back side marked portion involves a change of appearance or colour with respect to the non-marked portion of the same side of the retention base.

The marking of orthodontic aids in accordance with the invention can be produced along with the traditional marking by positioning said identification code both on the back and on the front side of these.

What is claimed is:

1. An orthodontic bracket, comprising:

a retention base for a respective tooth, said retention base having a back side; identifying indicia for identifying the respective tooth for which the orthodontic bracket is suitable, said indicia including a sign provided on the back side of said retention base, the size of said indicia being at least 3 square millimeters, the depth of said indicia being substantially null with respect to the depth of the retention base, said indicia having a profile which follows the outer profile of said retention base.

2. The orthodontic bracket according to claim 1, wherein said sign comprises character markings consisting of a number with two figures.

3. The orthodontic bracket according to claim 1, wherein said sign consists of a number with one figure preceded or followed by the plus sign or by a minus sign.

4. The orthodontic bracket according to claim 1, wherein said sign is provided on said back side of said retention base with a laser apparatus.

5. The orthodontic bracket according to claim 1, wherein said sign is provided on said back side of said retention base with a diode-pumped laser apparatus.

6. An orthodontic bracket, comprising:

a retention base for a respective tooth, said retention base having a net-like structured back side;

identifying indicia for identifying the respective tooth for which the orthodontic bracket is suitable, said indicia including a sign provided on the back side of said retention base, the size of said indicia being at least 3 square millimeters, the depth of said indicia being substantially null with respect to the depth of the retention base, said indicia having a profile which follows the outer profile of said retention base.

7. The orthodontic bracket according to claim 6, wherein said sign comprises character markings consisting of a number with two figures.

8. The orthodontic bracket according to claim 6, wherein said sign consists of a number with one figure preceded or followed by the plus sign or by a minus sign.

9. The orthodontic bracket according to claim 6, wherein said sign is provided on said back side of said retention base with a laser apparatus.

10. The orthodontic bracket according to claim 6, wherein said sign is provided on said back side of said retention base with a diode-pumped laser apparatus.

* * * * *